United States Patent [19]
Kajita et al.

[11] Patent Number: 5,238,775
[45] Date of Patent: Aug. 24, 1993

[54] RADIATION-SENSITIVE RESIN COMPOSITION

[75] Inventors: Toru Kajita; Takao Miura; Yoshiji Yumoto, all of Yokkaichi; Chozo Okuda, Chiba, all of Japan

[73] Assignee: Japan Synthetic Rubber Co., Ltd., Tokyo, Japan

[21] Appl. No.: 656,857

[22] Filed: Feb. 19, 1991

[30] Foreign Application Priority Data

Feb. 20, 1990 [JP] Japan .................................. 2-39409

[51] Int. Cl.$^5$ .......................... G03F 7/023; G03F 7/32
[52] U.S. Cl. ..................... 430/192; 430/165; 430/190; 430/191; 430/193; 430/326; 534/556; 534/557
[58] Field of Search ............... 430/191, 192, 193, 165, 430/166, 190; 534/556, 557

[56] References Cited

U.S. PATENT DOCUMENTS

| | | | |
|---|---|---|---|
| 3,046,118 | 7/1962 | Schmidt | 430/193 |
| 3,046,122 | 7/1962 | Süs | 430/193 |
| 4,266,001 | 5/1981 | Buhr et al. | 430/191 |
| 4,387,152 | 6/1983 | Stahlhofen | 430/192 |
| 4,424,270 | 1/1984 | Erdman et al. | 430/191 |
| 4,499,271 | 2/1985 | Hosalla et al. | 430/192 |
| 4,555,469 | 11/1985 | Erdmann et al. | 430/192 |
| 4,594,306 | 6/1986 | Stahlhofen et al. | 430/191 |
| 4,626,492 | 12/1986 | Eilbeck | 430/192 |
| 4,737,437 | 4/1988 | Gutsell, Jr. et al. | 430/192 |
| 4,738,915 | 4/1988 | Komine et al. | 430/191 |
| 4,837,121 | 6/1989 | Blakeney et al. | 430/165 |
| 5,112,719 | 5/1992 | Yamada et al. | 430/191 |

FOREIGN PATENT DOCUMENTS

| | | |
|---|---|---|
| 0358871 | 3/1990 | European Pat. Off. . |
| 0430477 | 6/1991 | European Pat. Off. . |
| 0435437 | 7/1991 | European Pat. Off. . |
| 63-14898 | 7/1989 | Japan . |

*Primary Examiner*—Charles L. Bowers, Jr.
*Assistant Examiner*—John S. Chu
*Attorney, Agent, or Firm*—Oliff & Berridge

[57] ABSTRACT

A radiation-sensitive resin composition containing an alkali-soluble resin, comprising a polyhydroxy compound having the following formula:

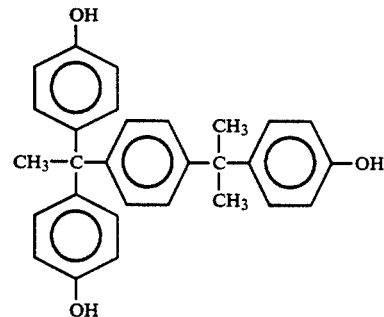

or a quinonediazidesulfonate of the polyhydroxy compound. The radiation-sensitive resin composition is suitable for use as a positive type photoresist which has such excellent developability as to inhibit effectively the generation of scum in the formation of a photoresist pattern, has high sensitivity and is excellent in heat resistance and remained thickness ratio upon development.

12 Claims, No Drawings

RADIATION-SENSITIVE RESIN COMPOSITION

BACKGROUND OF THE INVENTION

1. Field of the Invention

The present invention relates to a radiation-sensitive resin composition containing an alkali-soluble resin, and more particularly to a radiation-sensitive resin composition which is sensitive to such radiations as ultraviolet rays, far ultraviolet rays, X-rays, electron beams, molecular beams, gamma-rays, synchrotron radiations, proton beams, etc. and suitable for use as a photoresist for fabrication of highly integrated circuits.

2. Description of the Prior Art

Positive type photoresists are widely used in the manufacture of integrated circuits, because they give photoresist patterns with high resolution. With the recent trend toward integrated circuits of higher integration, however, there has been a growing demand for a positive type photoresist from which a photoresist pattern with a further enhanced resolution can be formed. That is, in the formation of a fine photoresist pattern by use of a positive type photoresist, it is required that the development of a latent image, formed by exposure, with a developing solution consisting of an aqueous alkaline solution should proceed rapidly to the area where the exposed portion adjoin a wafer (namely, the base portion of the pattern).

However, the conventional positive type photoresists have a developability problem in that when the interval of pattern elements of the photoresist pattern to be formed is 0.8 μm or below, an undeveloped residue called "scum" is liable to be left upon development.

In response to the increasing integration of integrated circuits, furthermore, the etching method for wafers has been changing from the conventional wet etching, which involves heavier side etching, to the dry etching with less side etching. In the dry etching, the photoresist pattern should not change during etching; therefore, the photoresist should have good heat resistance.

SUMMARY OF THE INVENTION

Accordingly, it is an object of the present invention to provide a radiation-sensitive resin composition suitable for use as a positive type photoresist which has such excellent developability as to inhibit effectively the generation of scum in the formation of a photoresist pattern, has high sensitivity and which is excellent in heat resistance and remained thickness ratio upon development.

According to the present invention, there is provided a radiation-sensitive resin composition containing an alkali-soluble resin, comprising a compound having the following general formula [I]:

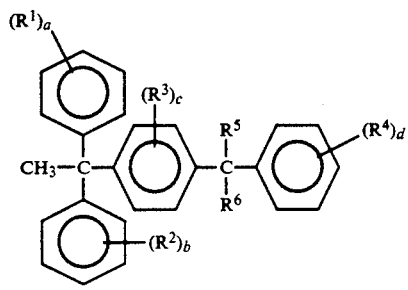

wherein $R^1$, $R^2$, $R^3$ and $R^4$ may be the same or different and each of $R^1$ to $R^4$ may comprise two or more different groups, and $R^1$ to $R^4$ are each a substituted or unsubstituted alkyl group, a substituted or unsubstituted aryl group or an OD group, wherein D is a hydrogen atom or an organic group containing a 1,2-quinonediazide group, at least one of $R^1$, $R^2$ and $R^4$ containing at least one OD group; $R^5$ and $R^6$ are each a hydrogen atom or a substituted or unsubstituted alkyl group; a, b and d are each an integer of from 0 to 5, provided at least one of a, b and d is a positive integer; and c is an integer of from 0 to 4.

The radiation-sensitive resin composition of the present invention can be used suitably as a positive type photoresist which has excellent developability such as to inhibit effectively the generation of scum in the formation of a photoresist pattern, has high sensitivity and is excellent in heat resistance and remained thickness ratio upon development.

DETAILED DESCRIPTION OF THE INVENTION

Alkali-soluble resin

The alkali-soluble resin for use in the present invention (the resin will be hereinafter referred to as "resin (A)") includes, for example, novolak resins, resol resins, polyvinylphenol and derivatives thereof, styrene-maleic anhydride copolymers, polyvinyl hydroxybenzoate, carboxyl group-containing methacrylic resins, etc., of which particularly preferred are novolak resins. Of the novolak resins, those obtained by polycondensation of a phenol having the following general formula [II]:

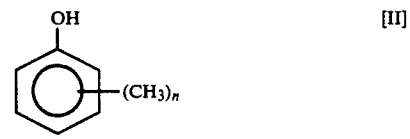

wherein n is an integer of from 1 to 3, with an aldehyde, are especially preferable.

Preferred examples of the phenol for preparation of the novolak resin include o-cresol, m-cresol, p-cresol, 2,3-xylenol, 2,4-xylenol, 2,5-xylenol, 2,6-xylenol, 3,4-xylenol, 3,5-xylenol, 2,3,4-trimethylphenol, 2,3,5-trimethylphenol, 3,4,5-trimethylphenol, and so on, of which preferred are o-cresol, m-cresol, p-cresol, 2,5-xylenol, 3,5-xylenol and 2,3,5-trimethylphenol. The phenols may be used either singly or in combination of one or more.

The aldehydes for polycondensation with the above phenols include, for example, formaldehyde, trioxane, paraformaldehyde, benzaldehyde, acetaldehyde, propylaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, o-methylbenzaldehyde, m-methylbenzaldehyde, p-methylbenzaldehyde, p-ethylbenzaldehyde, p-n-butylbenzaldehyde, furfural, etc., with formaldehyde being particularly preferable. These aldehydes may be used either singly or in combination of two or more.

The aldehyde is used preferably in an amount of from 0.7 to 3 moles, more preferably from 0.8 to 1.5 moles, per mole of the phenol.

In the polycondensation of the phenol and the aldehyde, generally, an acidic catalyst is used. The acidic catalysts usable include, for example, inorganic acids such as hydrochloric acid, nitric acid, sulfuric acid, etc., and organic acids such as formic acid, oxalic acid, acetic acid, etc. The amount of the acidic catalysts used is ordinarily from $1 \times 10^{-5}$ to $5 \times 10^{-1}$ mole per mole of the phenol.

In the polycondensation, generally, water is used as a reaction medium. However, where the phenol used for the polycondensation is insoluble in the aqueous solution of the aldehyde and therefore the reactants form a heterogeneous system from the beginning of the reaction, a hydrophilic solvent may also be used as the reaction medium. The hydrophilic solvents usable in such a case include, for example, alcohols such as methanol, ethanol, propanol, butanol, etc., and cyclic ethers such as tetrahydrofuran, dioxane, etc. The amount of the reaction medium is ordinarily from 20 to 1000 parts by weight per 100 parts by weight of the reactants.

The polycondensation temperature can be controlled suitably according to the reactivity of the reactants, and is generally from 10° to 200° C., preferably from 70° to 130° C.

The polycondensation may be carried out, for example, by a method in which the phenol, aldehyde, acidic catalyst and so on are placed in a reaction vessel at a time, or a method in which the phenol, aldehyde and so on are added gradually as the reaction proceeds.

After the polycondensation is finished, the temperature of the reaction system is generally raised to a temperature of from 130° to 230° C., in order to remove the unreacted reactants, the acidic catalyst, the reaction medium, etc. from the reaction system. Then, volatile components are distilled off under a reduced pressure, for instance from about 20 to 50 mmHg, and the resin (A) formed is recovered.

The weight average molecular weight in terms of polystyrene (hereinafter referred to as "Mw") of the resin (A) used in the present invention is preferably from 2,000 to 20,000, a more preferable range being from 3,000 to 15,000. When Mw exceeds 20,000, uniform application of the composition of the invention to a wafer may become difficult and, further, the developability and sensitivity of the composition are apt to be lowered. When Mw is below 2,000, on the other hand, the composition tends to be poor in heat resistance of the resist pattern to be obtained.

The resin (A) with a high Mw value can be obtained by dissolving the resin obtained as above in a good solvent such as ethyl cellosolve acetate, dioxane, methanol, ethyl acetate, etc., then adding a poor solvent such as water, n-hexane, n-heptane, etc. thereto, separating a resin solution layer thus formed, and recovering the resin (A) having a high molecular weight.

Compound (A) of the general formula [I]

The composition according to the present invention contains at least one of the compounds having the aforementioned general formula [I], namely:

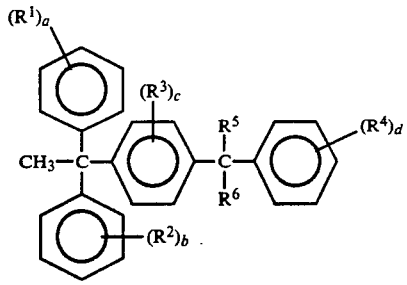

The compound of the general formula [I] includes a compound represented by the general formula [I] wherein all of the D's are hydrogen atoms (hereinafter referred to as "compound (A)" and derivatives of the Compound (A) represented by the general formula [I] wherein at least one of the D's is an organic group containing a 1,2-quinonediazide group (hereinafter referred to as "compound (B)").

In the general formula [I], the groups $R^1$ to $R^4$ are each a substituted or unsubstituted alkyl group, a substituted or unsubstituted aryl group or an OD group, wherein D is a hydrogen atom or an organic group containing a 1,2-quinonediazide group. The substituted or unsubstituted alkyl group includes, for example, methyl, ethyl, n-propyl, isopropyl, n-butyl, t-butyl, cyclohexyl, hydroxymethyl, chloromethyl, bromomethyl, 2-chloromethyl, trimethylsilylmethyl, benzyl and cumyl groups, etc., of which preferred are methyl, ethyl, hydroxymethyl and the like. The substituted or unsubstituted aryl group includes, for example, phenyl, 1-naphthyl, 2-naphthyl, 4-hydroxyphenyl, 4-trimethylsiloxyphenyl, 4-methoxyphenyl and 4-acetylphenyl groups, etc., of which preferred are phenyl, 4-hydroxylphenyl and the like.

The organic group containing a 1,2-quinonediazide group includes, for example, 1,2-benzoquinonediazide-4-sulfonyl group, 1,2-naphthoquinonediazide-5-sulfonyl group, 1,2-naphthoquinonediazide-4-sulfonyl group, 2,1-naphthoquinonediazide-5-sulfonyl group, 2,1-naphthoquinonediazide-4-sulfonyl group and so on, of which preferred are the 1,2-naphthoquinonediazide-4-sulfonyl and 1,2-naphthoquinonediazide-5-sulfonyl groups and the like.

The groups $R^1$ to $R^4$ bonded to respective benzene rings may be the same or different and each of $R^1$ to $R^4$ may comprise two or more different groups, and at least one of the groups $R^1$, $R^2$ and $R^4$ contains at least one OD group.

The groups $R^5$ and $R^6$ are each a hydrogen atom or a substituted or unsubstituted alkyl group. Examples of the substituted or unsubstituted alkyl group include methyl, ethyl, n-propyl, isopropyl, n-butyl, t-butyl, cyclohexyl, hydroxymethyl, chloromethyl, bromomethyl, 2-chloromethyl, trimethylsilylmethyl, benzyl and cumyl groups, etc., of which preferred are methyl, ethyl and hydroxymethyl groups and the like.

Specific examples of the compound (A) having the general formula (I) (the compound (A) corresponds to the case where at least one of the aforementioned OD groups is the hydroxyl group) include the followings:

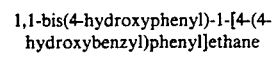

1,1-bis(4-hydroxyphenyl)-1-[4-(4-hydroxybenzyl)phenyl]ethane

-continued

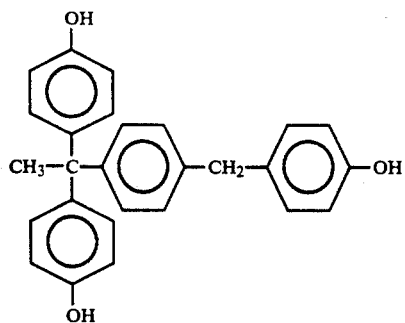

1,1-bis(3,5-dimethyl-4-hydroxyphenyl)-1-[4-(4-hydroxybenzyl)phenyl]ethane

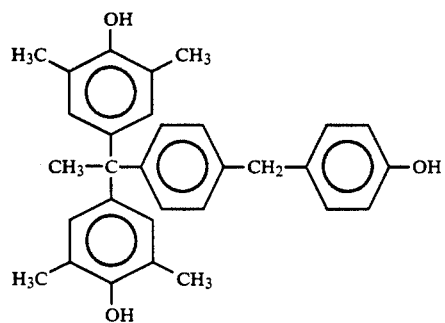

1,1-bis(3,5-dimethyl-2-hydroxyphenyl)-1-[4-(4-hydroxybenzyl)phenyl]ethane

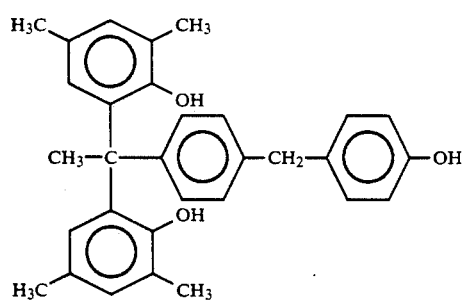

1,1-bis(4-hydroxy-3-methylphenyl)-1-[4-(4-hydroxybenzyl)phenyl]ethane

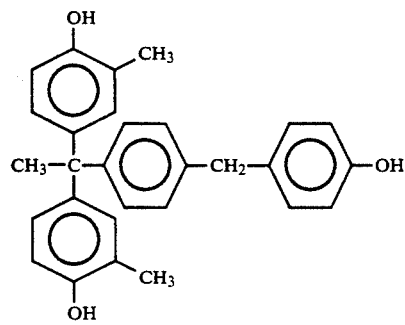

1,1-bis(2,6-dimethyl-4-hydroxyphenyl)-1-[4-(4-hydroxybenzyl)phenyl]ethane

-continued

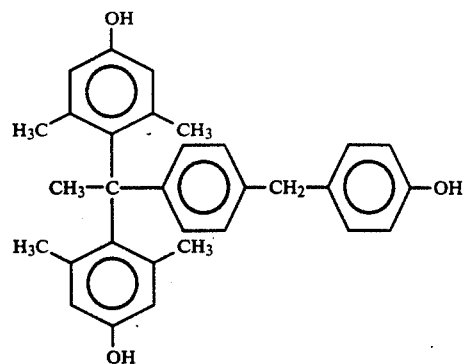

1,1-bis(3,4-dihydroxyphenyl)-1-[4-(4-hydroxybenzyl)phenyl]ethane

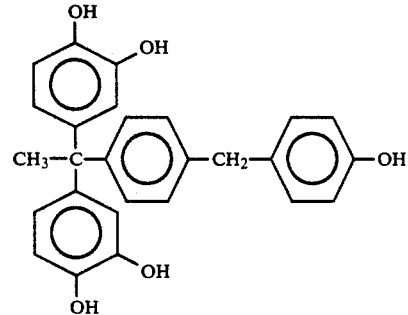

1,1-bis(2,3,4-trihydroxyphenyl)-1-[4-(4-hydroxybenzyl)phenyl]ethane

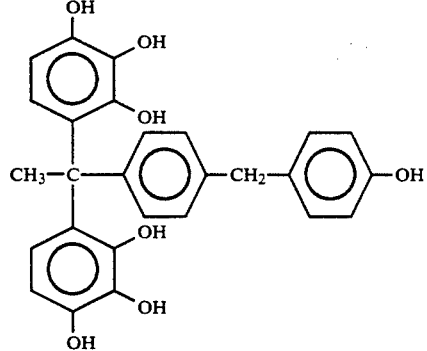

1,1-bis(4-hydroxyphenyl)-1-[4-{1-(4-hydroxyphenyl)-1-methylethyl}phenyl]ethane

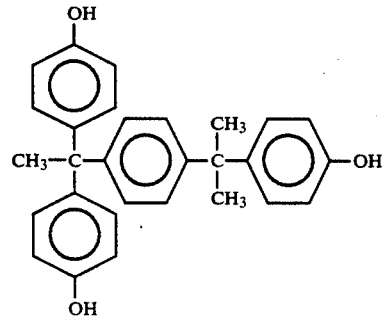

1,1-bis(3,5-dimethyl-4-hydroxyphenyl)-1-[4-{1-(4-hydroxyphenyl)-1-methylethyl}phenyl]ethane -continued

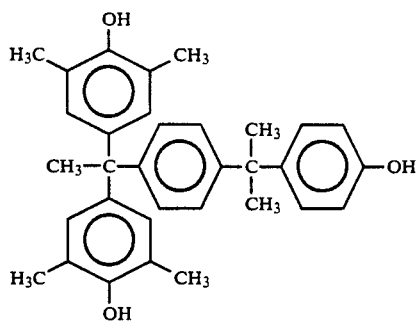

1,1-bis(3,5-dimethyl-2-hydroxyphenyl)-1-[4-{1-(4-hydroxyphenyl)-1-methylethyl}phenyl]ethane

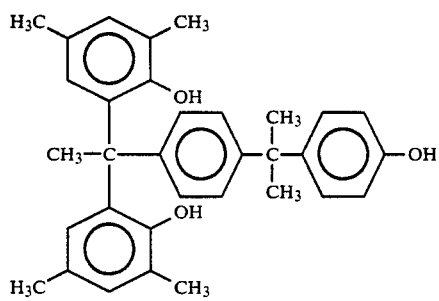

1,1-bis(4-hydroxy-3-methylphenyl)-1-[4-{1-(4-hydroxyphenyl)-1-methylethyl}phenyl]ethane

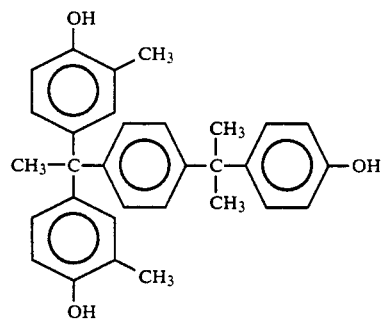

1,1-bis(2,6-dimethyl-4-hydroxyphenyl)-1-[4-{1-(4-hydroxyphenyl)-1-methylethyl}phenyl]ethane

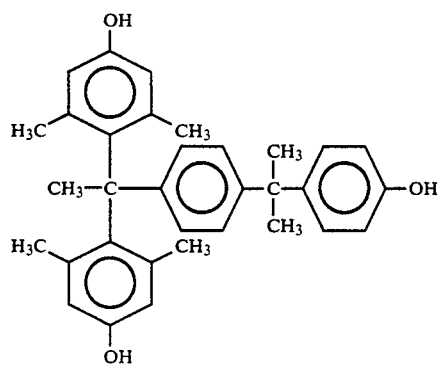

1,1-bis(3,4-dihydroxyphenyl)-1-[4-{1-(4-hydroxyphenyl)-1-methylethyl}phenyl]ethane -continued

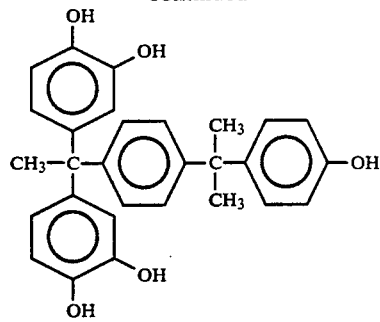

1,1-bis(2,3,4-trihydroxyphenyl)-1-[4-{1-(4-hydroxyphenyl)-1-methylethyl}phenyl]ethane

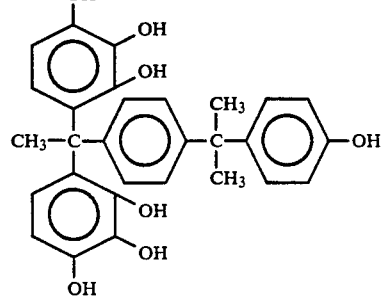

The aforementioned compound (A) can be obtained by condensation of a substituted or unsubstituted phenol with a substituted acetophenone in the presence of an acidic catalyst, as for instance disclosed in German Patent No. 1,930,333 (Federal Republic). The reaction product is obtained generally as an oily mixture, which may be purified by recrystallization, for instance.

The compound (B) is a compound obtained by substituting part or the whole of the hydroxyl groups contained in the compound (A) by an organic group containing a 1,2-quinonediazide group. The compound (B) can be obtained, for example, by esterification of the aforementioned compound (A) with a 1,2-naphthoquinonediazidesulfonyl halide such as 1,2-naphthoquinonediazide-4-sulfonyl chloride, 1,2-naphthoquinonediazide-5-sulfonyl chloride, etc.

In the present invention, in order that the developability-improving effect of the compound (B) may be attained satisfactorily, the average percentage of condensation upon the esterification, defined as [(the number of phenolic hydroxyl groups esterified)/(the number of phenolic hydroxyl groups before reaction)] × 100 and hereinafter referred to as "average condensation degree", is generally 100% or below, preferably 50% or below, and more preferably 30% or below.

In the present invention, the compound (A) or compound (B) as mentioned above is used preferably in an amount of from 0.5 to 90 parts by weight, more preferably from 2 to 50 parts by weight, per 100 parts by weight of the resin (A).

1,2-Quinone diazide compound

In the present invention, where the compound (B) is not used, it is necessary to use a 1,2-quinone diazide compound other than the compound (B). Where the compound (B) is used, a 1,2-quinone diazide compound other than the compound (B) can be used in the composition of the invention. Such 1,2-quinone diazide compounds include, for example, 1,2-benzoquinonediazide- 4-sulfonates, 1,2-naphthoquinonediazide-4-sulfonates, 1,2-naphthoquinonediazide-5-sulfonates, etc. More specific examples of the usable 1,2-quinone diazide compounds are 1,2-benzoquinonediazide-4-sulfonates, 1,2-naphthoquinonediazide-4-sulfonates and 1,2-naphthoquinonediazide-5-sulfonates of (poly)hydroxybenzenes such as p-cresol, resorcinol, pyrogallol, phloroglucinol, etc.; 1,2-benzoquinonediazide-4-sulfonates, 1,2-naphthoquinonediazide-4-sulfonates and 1,2-naphthoquinonediazide-5-sulfonates of (poly)hydroxyphenyl alkyl ketones or (poly)hydroxyphenyl aryl ketones such as 2,4-dihydroxyphenyl propyl ketone, 2,4-dihydroxyphenyl n-hexyl ketone, 2,4-dihydroxybenzophenone, 2,3,4-trihydroxyphenyl n-hexyl ketone, 2,3,4-trihydroxybenzophenone, 2,4,6-trihydroxybenzophenone, 2,3,4,4'-tetrahydroxybenzophenone, 2,2',3,4'-tetrahydroxybenzophenone, 3'-methoxy-2,3,4,4'-tetrahydroxybenzophenone, 2,2',4,4'-tetrahydroxybenzophenone, 2,2',3,4,6'-pentahydroxybenzophenone, 2,3,3',4,4',5'-hexahydroxybenzophenone, 2,3',4,4',5',6-hexahydroxybenzophenone, etc.; 1,2-benzoquinonediazide-4-sulfonates, 1,2-naphthoquinonediazide-4-sulfonates and 1,2-naphthoquinonediazide-5-sulfonates of bis[(poly)hydroxyphenyl]alkanes such as bis(4-hydroxyphenyl)methane, bis(2,4-dihydroxyphenyl)methane, bis(2,3,4-trihydroxyphenyl)methane, 2,2-bis(4-hydroxyphenyl)propane, 2,2-bis(2,4-dihydroxyphenyl)propane 2,2-bis(2,3,4-trihydroxyphenyl)propane, 1,1-bis(4-hydroxyl)-1-phenylethane, 1,1,1-tris(4-hydroxyphenyl)ethane, etc.; 1,2-benzoquinonediazide-4-sulfonates, 1,2-naphthoquinonediazide-4-sulfonates and 1,2-naphthoquinonediazide-5-sulfonates of alkyl (poly)hydroxybenzoates or aryl (poly)hydroxybenzoates such as lauryl 3,5-dihydroxybenzoate, phenyl 2,3,4-trihydroxybenzoate, lauryl 3,4,5-trihydroxybenzoate, propyl 3,4,5-trihydroxybenzoate, phenyl 3,4,5-trihydroxybenzoate, etc.; 1,2-benzoquinonediazide-4-sulfonates, 1,2-naphthoquinonediazide-4-sulfonates and 1,2-naphthoquinonediazide-5-sulfonates of bis(polyhydroxybenzoyl)alkanes such as bis(2,5-dihydroxybenzoyl)methane, bis(2,3,4-trihydroxybenzoyl)methane and bis(2,4,6-trihydroxybenzoyl)methane, or bis(polyhydroxybenzoyl)benzenes such as p-bis(2,5-dihydroxybenzoyl)benzene, p-bis(2,3,4-trihydroxybenzoyl)benzene, p-bis(2,4,6-trihydroxybenzoyl)benzene; and 1,2-benzoquinonediazide-4-sulfonates, 1,2-naphthoquinonediazide-4-sulfonates and 1,2-naphthoquinonediazide-5-sulfonates of polyethylene glycol di[(poly)hydroxybenzoates] such as ethylene glycol di(3,5-dihydroxybenzoate), polyethylene glycol di(3,5-dihydroxybenzoate), polyethylene glycol di(3,4,5-trihydroxybenzoate), etc.; and 1,2-benzoquinonediazide-4-sulfonates, 1,2-naphthoquinonediazide-4-sulfonates and 1,2-naphthoquinonediazide-5-sulfonates of phenol resins, and so on.

Of the aforementioned 1,2-quinone diazide compounds, particularly preferred are polyhydroxybenzophenone 1,2-naphthoquinonediazidesulfonates such as 2,3,4-trihydroxybenzophenone 1,2-naphthoquinonediazide-4-sulfonate, 2,3,4-trihydroxybenzophenone 1,2-naphthoquinonediazide-5-sulfonate, 2,3,4,4'-tetrahydroxybenzophenone 1,2-naphthoquinonediazide-4sulfonate, 2,3,4,4'-tetrahydroxybenzophenone 1,2-naphthoquinonediazide-5-sulfonate, 3'-methoxy-2,3,4,4'-tetrahydroxybenzophenone 1,2-naphthoquinonediazide-4-sulfonate, 3'-methoxy-2,3,4,4'-tetrahydroxybenzophenone 1,2-naphthoquinonediazide-5-sulfonate, 1,1,1-tris(4-hydroxyphenyl)ethane 1,2-naphthoquinonediazide-5-sulfonate, etc., and 1,2-quinonediazidesulfonates obtained by sustituting, for instance, from 20 to 100 mol %, preferably from 40 to 100 mol %, of the hydrogen atoms of the hydroxyl groups contained in a novlak resin or resol resin (hereinafter referred to simply as "resin (B)") by a 1,2-quinonediazidesulfonyl group such as 1,2-naphthoquinonediazide-4-sulfonate group, 1,2-naphthoquinonediazide-5-sulfonate group, etc.

The resin (B) can be obtained by condensation of a phenol and an aldehyde. The phenols usable for the condensation include phenol, 1-naphthol, 2-naphthol and the like, as well as those phenols mentioned above for use in synthesis of the resin (A). As the aldehyde for the condensation, also, those aldehydes usable in synthesis of the resin (A) can be used. Such an aldehyde is used preferably in an amount of from 0.1 to 3 moles, more preferably from 0.2 to 1.5 moles, per mole of the phenol used. In the condensation, further, alkaline catalysts as well as those acidic catalysts usable for synthesis of the resin (A) can be used.

Generally, the Mw of the resin (B) is preferably not more than 10,000, more preferably from 200 to 2,000 in view of easiness of esterification and solubility in solvents. An especially preferred Mw value ranges from 300 to 1,000. The 1,2-quninonediazidesulfonates of the resin (B) include, for example, 1,2-benzoquinonediazide-4-sulfonates, 1,2-naphthoquinonediazide-4-sulfonates and 1,2-naphthoquinonediazide-5-sulfonates of phenol/formaldehyde condensed novolak resins, m-cresol/formaldehyde condensed novolak resins, p-cresol/formaldehyde condensed novolak resins, o-cresol/formaldehyde condensed novolak resins, m-cresol/p-cresol/formaldehyde condensed novolak resins, etc.

In the composition of the present invention, the amount of the 1,2-quinone diazide compound is generally from 3 to 100 parts by weight, preferably from 5 to 50 parts by weight, per 100 parts by weight of the resin (A), with the total amount of the 1,2-quinonediazidesulfonyl groups in the composition being controlled to within the range of generally from 5 to 25% by weight, preferably from 10 to 20% by weight.

Other compounding agents

The composition according to the present invention can further comprise various compounding agents such as sensitizer, surface active agent, dissolution accelerator, etc.

Sensitizers can be incorporated in the composition, in order to enhance sensitivity of the composition. Such sensitizers include, for example, 2H-pyrido-(3,2-b)-1,4-oxazin-3(4H)-ones, 10H-pyrido-(3,2-b)-(1,4)-benzothiazines, urazols, hydantoins, barbituric acids, glycine anhydrides, 1-hydroxybenzotriazoles, alloxans, maleimides, etc. The amount of the sensitizers used is generally up to 50 parts by weight per 100 parts by weight of the resin (A).

Surface active agents can be incorporated in the composition, for improving the application properties or developing properties of the composition. The usable surface active agents include, for example, polyoxyethylene lauryl ether, polyoxyethylene stearyl ether, polyoxyethylene oleyl ether, polyoxyethylene octylphenyl ether, polyoxyethylene nonylphenyl ether, polyethylene glycol dilaurate, polyethylene glycol distearate, etc.; F-Top EF301, EF303 and EF352 (tradenames for products by Shin-Akita Kasei K.K.), Megafac F171, F172 and F173 (tradenames for products by Dainippon Ink & Chemicals, Inc.), Fluorad FC430 and FC431 (tradenames for products by Sumitomo 3M Co., Ltd.), Asahi Guard AG710, Surflon S-382, SC-101, SC-102, SC-103, SC-104, SC-105 and SC-106 (tradenames for products by Asahi Glass Co., Ltd.), etc.; organosiloxane polymer KP341 (tradename for a product by Shin-Etsu Chemical Co., Ltd.); acrylic or methacrylic (co)polymers Polyflow No. 75 and No. 95 (tradenames for products by Kyoeisha Chemical Co., Ltd.), etc.

The amount of the surface active agent used is generally 2 parts by weight or less per 100 parts by weight of solid components in the composition.

Dissolution accelerators can be incorporated in the composition, in order to accelerate dissolution of the composition in the developing solution and to improve the sensitivity and developing properties of the composition. Such dissolution accelerators include, for example, 1,1-bis(4-hydroxyphenyl)-1-phenylethane, 1,1,1-tris(4-hydroxyphenyl)ethane, 3,5-dimethyl-4,4'-dihydroxydiphenylmethane, bisphenol A, 3,5-dimethyl-2',4-dihydroxydiphenylmethane, 1,1-bis(4-hydroxyphenyl)-cyclohexane, 1,1-bis(4-hydroxyphenyl)-4-methylcyclohexane, alkali-soluble novolak resins having a weight average molecular weight in terms of polystyrene of 2,000 or less, etc. The amount of the dissolution accelerators used is generally up to 50 parts by weight per 100 parts by weight of the resin (A).

In the composition of the present invention, furthermore, a dye or pigment may be incorporated in order to visualize a latent image in the area irradiated with radiations and to reduce the influence of halation upon the irradiation. Also, an adhesion aid can be incorporated in the composition in order to improve the adhesion of the composition. Moreover, stabilizer, defoaming agent, etc. may also be incorporated in the composition, as required.

Preparation of the composition and formation of pattern

The composition of the present invention is prepared, for example, by dissolving the resin (A) and the compound (A) or compound (B), optionally with 1,2-quinone diazide compounds and other compounding agents as required, in a solvent so as to obtain a solids content of, for example, from 20 to 40% by weight, and filtrating the resultant solution through a filter having a pore diameter of about 0.2 μm.

Examples of the solvent for use here include ethylene glycol monomethyl ether, ethylene glycol monoethyl ether, methyl cellosolve acetate, ethyl cellosolve acetate, etc.; diethylene glycol monomethyl ether, diethylene glycol monoethyl ether, propylene glycol methyl ether acetate, propylene glycol propyl ether acetate, toluene, xylene, methyl ethyl ketone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, ethyl acetate, butyl acetate, methyl 3-methoxypropionate, ethyl 3-methoxypropionate, ethyl 3-ethoxypropionate, methyl 3-ethoxypropionate, etc. These solvents may be used either singly or in combination of two or more. Furthermore, high boiling point solvents can also be added, such as N-methylformamide, N,N-dimethylformamide, N-methylformanilide, N-methylacetamide, N,N-dimethylacetamide, N-methylpyrrolidone, dimethyl sulfoxide, benzyl ethyl ether, dihexyl ether, acetonylacetone, isophorone, caproic acid, caprylic acid, 1-octanol, 1-nonanol, benzyl alcohol, benzyl acetate, ethyl benzoate, diethyl oxalate, diethyl maleate, gammabutyrolactone, ethylene carbonate, propylene carbonate, phenyl cellosolve acetate, etc.

The composition of the present invention is applied by spin coating, flow-coating, roll coating or the like to, for example, a silicon wafer or a wafer having a coating of aluminum or the like thereon, whereby a photosensitive layer is formed. The photosensitive layer is then irradiated with radiations through a predetermined mask pattern, followed by development with a developing solution to form a pattern.

Where the composition of the present invention is used as a positive type photoresist, the effect of the invention can be further enhanced by applying the composition to a wafer or the like, subjecting the applied composition to prebaking and exposure, and then heating the composition at a temperature of from 70° to 140° C., followed by development.

Developing solution

As the developing solution for the composition of the present invention, aqueous alkaline solutions are used which contain an alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, choline, pyrrole, piperidine, 1,8-diazabicyclo-(5,4,0)-7-undecene, 1,5-diazabicyclo-(4,3,0)-5-nonane, etc., in a concentration of generally from 1 to 10% by weight, preferably from 2 to 5% by weight.

To the developing solution, furthermore, water-soluble organic solvents, for example, alcohols such as methanol, ethanol, etc., or surface active agents may also be added in appropriate amounts.

The development of a latent image with the developing solution consisting of the aqueous alkaline solution as above is, in general, followed by rinsing in water.

EXAMPLES

The present invention will now be explained more in detail by referring to the following examples, which are not to be construed as limitative of the invention.

In the examples, measurement of Mw and evaluation of photoresists were carried out as follows.

Mw

Mw was measured by gel permeation chromatography with monodisperse polystyrene as a standard, using GPC columns (two G2000H$_6$ columns, one G3000H$_6$ column and one G4000H$_6$ column, produced by Toyo Soda Mfg. Co., Ltd.) under the conditions of a flow rate of 1.5 ml/min, a column temperature of 40° C. and with tetrahydrofuran as eluent.

Sensitivity

Exposure was carried out on a Model NSR-1505G4D step and repeat reduction projection aligner (numerical aperture: 0.45, a product by Nikon Corp.) using g-line of a wavelength of 436 nm, with the exposure time varied, or on a Model NSR-1505i6A step and repeat reduction projection aligner (numerical aperture: 0.45, a product by Nikon Corp.) using i-line of a wavelength of 365 nm, with the exposure time varied. After the exposure, development was carried out using a 2.4 wt. % aqueous solution of tetramethylammonium hydroxide as a developing solution at 25° C. for 60 seconds, followed by rinsing with water and drying to form a photoresist pattern on a wafer. An exposure time suitable for forming a 0.6-μm line-and-space pattern (1L/1S pattern) in a width ratio of 1:1 was determined (this exposure time will be hereinafter referred to as "optimum exposure time").

Resolution

The minimum size of photoresist patterns resolved upon exposure for the optimum exposure time was measured.

Remained thickness ratio upon development

The thickness of a pattern developed after exposure for the optimum exposure time was divided by the photoresist film thickness before the development, then the resultant quotient was multiplied by 100, and the value thus obtained was presented with the percent symbol, %.

Developability

The extent of scumming or residue left upon development was examined.

Heat resistance

A wafer provided thereon with a photoresist pattern was placed in a clean oven to determine the temperature at which the pattern started being deformed.

Pattern shape

After development of a 0.6-μm photoresist pattern, the upper edge A and the lower edge B of the developed portion, generally rectangular in section, were measured under a scanning electron microscope. The pattern shape was judged as good when the A and B values of the pattern satisfied the relationship: $0.85 \leq B/A \leq 1$. When the sectional contour of the pattern trailed at its foot or reversely tapered, the pattern shape was judged as bad, even if the value of B/A was in the above range.

SYNTHESIS OF RESIN (A)

Synthesis Example 1

A flask equipped with a stirrer, a cooling pipe and a thermometer was charged with 67.6 g (0.63 mol) of m-cresol, 10.0 g (0.073 mol) of 2,3,5-trimethylphenol, 31.8 g (0.29 mol) of p-cresol, 107.1 g of a 37 wt. % aqueous solution of formaldehyde (formaldehyde: 1.32 mol) and 1.33 g ($1.06 \times 10^{-2}$ mol) of oxalic acid dihydrate. With the flask immersed in an oil bath to maintain the temperature inside the flask at 100° C., polycondensation was carried out with stirring for 30 minutes. Then, 17.5 g (0.16 mol) of m-cresol and 40.0 g (0.29 mol) of 2,3,5-trimethylphenol were added to the flask, and polycondensation was further carried out for 40 minutes.

Next, the oil bath temperature was raised to 180° C. and, simultaneously, the pressure inside the flask was reduced to a value of from 30 to 50 mmHg, thereby removing water, oxalic acid and the unreacted formaldehyde, m-cresol, p-cresol and 2,3,5-trimethylphenol.

The molten resin thus obtained was recovered by cooling back to room temperature. The resin obtained will be referred to as "resin (A1)".

Synthesis Example 2

The resin (A1) was dissolved in ethyl cellosolve acetate so as to attain a solids content of 20% by weight. To one part by weight of the resin solution thus obtained, two parts by weight of methanol and one part by weight of water were added, followed by stirring, and the stirred admixture was left to stand. After the admixture separated into two layers by being left to stand, the resin solution layer (lower layer) was taken out, concentrated, dehydrated and dried, whereby the resin was recovered. The resin thus obtained will be referred to as "resin (A2)".

Synthesis Example 3

An autoclave was charged with 69.2 g (0.64 mol) of m-cresol, 21.8 g (0.16 mol) of 2,3,5-trimethylphenol, 61.0 g of a 37 wt. % aqueous solution of formaldehyde (formaldehyde: 0.75 mol), 6.3 g (0.05 mol) of oxalic acid dihydrate, 52.6 g of water and 182 g of dioxane. With the autoclave immersed in an oil bath to maintain the temperature inside the autoclave at 130° C., condensation was carried out with stirring for 6 hours. After the reaction, the temperature was returned to room temperature, and the reaction mixture of the autoclave was removed into a beaker. After the reaction mixture in the beaker separated into two layers, the lower layer was taken out, concentrated, dehydrated and dried, whereby a resin was recovered. The resin obtained will be referred to as "resin (A3)".

Synthesis Example 4

A flask similar to that used in Synthesis Example 1 was charged with 13.0 g (0.12 mol) of m-cresol, 32.4 g (0.3 mol) of p-cresol, 39.0 g (0.32 mol) of 3,5-xylenol, 56.9 g of a 37 wt. % aqueous solution of formaldehyde (formaldehyde: 0.70 mol) and 0.083 g ($6.59 \times 10^{-4}$ mol) of oxalic acid dihydrate. With the flask immersed in an oil bath to maintain the temperature inside the flask at 100° C., polycondensation was carried out with stirring for 30 minutes. Then, polycondensation was carried out further for 45 minutes, with continuous and gradual addition of 51.9 g (0.48 mol) of m-cresol and 9.77 g (0.08 mol) of 3,5-dimethylphenol to the flask according to the progress of the reaction.

Thereafter, the resin formed was recovered in the same manner as in Synthesis Example 1. The resin thus obtained will be referred to as "resin (A4)".

Synthesis Example 5

An autoclave was charged with 69.2 g (0.64 mol) of m-cresol, 19.5 g (0.16 mol) of 3,5-xylenol, 58.4 g of a 37 wt. % aqueous solution of formaldehyde (formaldehyde: 0.72 mol), 0.90 g ($7.14 \times 10^{-3}$ mol) of oxalic acid dihydrate, 54.4 g of water and 228 g of dioxane. Polycondensation was carried out or 10 hours, and the resultant resin was recovered in the same manner as in Synthesis Example 3. The resin obtained will be referred to as "resin (A5)".

Synthesis Example 6

A flask similar to that used in Synthesis Example 1 was charged with 26.0 g (0.24 mol) of m-cresol, 78.2 g (0.64 mol) of 3,5-xylenol, 146 g of a 37 wt. % aqueous solution of formaldehyde (formaldehyde: 1.80 mol) and 0.164 g ($1.30 \times 10^{-3}$ mol) of oxalic acid dihydrate. With the flask immersed in an oil bath to maintain the temperature inside the flask at 100° C., polycondensation was carried out with stirring for 30 minutes. Then, 104 g (0.96 mol) of m-cresol and 20.0 g (0.16 mol) of 3,5-xylenol were further added to the flask, and the contents of the flask was reacted further for 70 minutes.

Next, the oil bath temperature was raised to 180° C. and, simultaneously, the pressure inside the flask was reduced to a value of from 30 to 40 mm Hg, thereby removing water, oxalic acid and the unreacted formaldehyde, m-cresol and 3,5-xylenol. Subsequently, the resin thus formed was recovered in the same manner as in Synthesis Example 1. The resin obtained will be referred to as "resin (A6)".

Synthesis Example 7

A flask similar to that used in Synthesis Example 1 was charged with 95.2 g (0.88 mol) of m-cresol, 24.4 g (0.18 mol) of 2,3,5-trimethylphenol, 154 g of a 37 wt. % aqueous solution of formaldehyde (formaldehyde: 1.90 mol) and 1.82 g (0.014 mol) of oxalic acid dihydrate. With the flask immersed in an oil bath to maintain the temperature inside the flask at 100° C., polycondensation was carried out with stirring for 90 minutes. Then, 23.8 g (0.22 mol) of m-cresol and 97.6 g (0.72 mol) of 2,3,5-trimethylphenol were further added to the flask, and the contents of the flask was reacted further for 60 minutes.

Next, the oil bath temperature was raised to 180° C. and, simultaneously, the pressure inside the flask was reduced to a value of from 30 to 40 mm Hg, thereby removing water, oxalic acid and the unreacted formaldehyde, m-cresol and 2,3,5-trimthylphenol. Subsequently, the resin thus formed was recovered in the same manner as in Synthesis Example 1. The resin obtained will be referred to as "resin (A7)".

Synthesis Example 8

The resin (A7) was dissolved in ethyl cellosolve acetate so as to attain a solids content of 20% by weight. To one parts by weight of the resin solution thus formed, 1.8 parts by weight of methanol and one part by weight of water were added, followed by stirring, and the stirred admixture was left to stand. After the admixture separated into two layers by being left to stand, the resin solution layer (lower layer) was taken out, concentrated, dehydrated and dried, whereby a resin was recovered. The resin thus obtained will be referred to as "resin (A8)".

SYNTHESIS OF RESIN (B)

Synthesis Example 9

A flask similar to that used in Synthesis Example 1 was charged with 108.0 g (1.00 mol) of m-cresol, 24.3 g of a 37 wt. % aqueous solution of formaldehyde (formaldehyde: 0.30 mol) and 0.30 g ($2.40 \times 10^{-3}$ mol) of oxalic acid dihydrate. With the flask immersed in an oil bath to maintain the temperature inside the flask at 100° C., polycondensation was carried out for 40 minutes. Then, the resin thus formed was recovered in the same manner as in the synthesis of resin (A1). The resin thus recovered will be referred to as "resin (B1)".

Synthesis Example 10

A flask similar to that used in Synthesis Example 1 was charged with 64.9 g (0.60 mol) of m-cresol, 43.3 g (0.40 mol) of p-cresol, 20.3 g of a 37 wt. % aqueous solution of formaldehyde (formaldehyde: 0.25 mol) and 0.30 g ($2.40 \times 10^{-3}$ mol) of oxalic acid dihydrate. With the flask immersed in an oil bath to maintain the temperature inside the flask at 100° C., polycondensation was carried out with stirring for 30 minutes. The resin thus formed was then recovered in the same manner as in Synthesis Example 1. The resin obtained will be referred to as "resin (B2)".

ABBREVIATION OF COMPOUND (A)

Abbreviations will be hereinafter used for the following compounds, which each are included in the aforementioned compound (A):

1,1-bis(4-hydroxyphenyl)-1-[4-{1-(4-hydroxyphenyl)-1methylethyl}phenyl]ethane will be referred to simply as "compound (A1)", and 1,1-bis(4-hydroxyphenyl)-1-[4-(4- hydroxybenzyl) phenyl]ethane as "compound (A2)".

SYNTHESIS OF COMPOUND (B)

Synthesis Example 11

A flask equipped with a stirrer, a dropping funnel and a thermometer was charged with 42.5 g (0.10 mol) of the compound (A1), 53.7 g (0.20 mol) of 1,2-naphthoquinonediazide-5-sulfonic acid chloride and 100 g of dioxane, under shielding from light, and the contents of the flask was stirred to effect dissolution.

Next, the flask was immersed in a water bath controlled to a temperature of 30° C. When the temperature inside the flask attained a steady value of 30° C., 22.3 g (0.22 mol) of triethylamine was slowly added dropwise to the solution in the flask through the dropping funnel in such a way that the temperature would not exceed 35° C.

Thereafter, precipitates of triethylamine hydrochloride were removed by filtration, and the filtrate was poured into a large amount of diluted hydrochloric acid, to permit precipitation. The precipitates thus formed were then collected by filtration, and dried a whole day and night in a heating vacuum dryer controlled to 40° C., to yield a compound. The compound obtained will be referred to as "compound (B1)".

Synthesis Example 12

A compound (B2) was obtained in the same manner as in Synthesis Example 11 except that 42.5 g (0.10 mol) of the compound (A1), 67.2 g (0.25 mol) of 1,2-naphthoquinonediazide-5-sulfonic acid chloride and 27.8 g (0.275 mol) of triethylamine were used.

Synthesis Example 13

A compound (B3) was obtained in the same manner as in Synthesis Example 11 except that 42.5 g (0.10 mol) of the compound (A1), 53.7 g (0.20 mol) of 1,2-naphthoquiononediazide-4-sulfonic acid chloride and 22.3 g (0.22 mol) of triethylamine were used.

Synthesis Example 14

A compound (B4) was obtained in the same manner as in Synthesis Example 11 except that 39.6 g (0.10 mol) of the compound (A2), 53.7 g (0.20 mol) of 1,2-naphthoquinonediazide-5-sulfonic acid chloride and 22.3 g (0.22 mol) of triethylamine were used.

SYNTHESIS OF 1,2-QUINONE DIAZIDE COMPOUND

Synthesis Example 15

A quinone diazide compound (I) was obtained in the same manner as in Synthesis Example 11 except that 10.0 g of the resin (B1), 13.9 g of 1,2-naphthoquinonediazide-4-sulfonic acid chloride and 5.75 g of triethylamine were used.

Synthesis Example 16

A quinone diazide compound (II) was obtained in the same manner as in Synthesis Example 11 except that 10.0 g of the resin (B2), 16.6 g of 1,2-naphthoquinonediazide-5-sulfonic acid chloride and 6.86 g of triethylamine were used.

Examples 1 to 15, and Comparative Examples 1 to 3

In each example, a resin (A), a quinone diazide compound, a compound (A) or compound (B), and a solvent were mixed together to form a uniform solution, which was filtered through a membrane filter with 0.2 μm pore diameter to prepare a solution of the composition according to the present invention.

The solution thus obtained was applied by a spin coater to a silicon wafer having a silicon oxide film thereon. The solution thus applied was prebaked on a hot plate at 90° C. for 2 minutes to form a photoresist film 1.2 μm thick. Then, as mentioned above, the photoresist film was subjected to exposure, by irradiation with radiations at a wavelength of 436 nm (g-line) or 365 nm (i-line) through a reticle, and then to development, rinsing and drying. Thereafter, the photoresist film was evaluated as to sensitivity, resolution, remained thickness ratio upon development, developability, heat resistance and pattern shape. The results are shown in Table 1, together with the resins and the like used.

In Examples 1 to 11 and Comparative Examples 1 and 2, the exposure was carried out by irradiating with g-line, whereas i-line was used for the same purpose in Examples 12 to 15 and Comparative Example 3.

TABLE 1

| | Resin A | | | Quinonediazide[2] compound | | Compound (A) or Compound (B) | | Dissolution[3] accelerator | | Solvent[4] | |
|---|---|---|---|---|---|---|---|---|---|---|---|
| | Kind | Mw | Amount[1] | Kind | Amount[1] | Kind | Amount[1] | Kind | Amount[1] | Kind | Amount[1] |
| Examples | | | | | | | | | | | |
| 1 | A1 | 4300 | 100 | II/V | 7.5/20 | A1 | 5 | — | — | α | 320 |
| 2 | A1 | 4300 | 100 | IV | 25 | B2 | 5 | — | — | β | 320 |
| 3 | A4 | 4500 | 100 | III/V | 12.5/12.5 | A2 | 5 | — | — | α | 320 |
| 4 | A6 | 3700 | 100 | V | 20 | B3 | 7.5 | — | — | α | 320 |
| 5 | A7 | 4000 | 100 | V | 25 | A1 | 5 | — | — | α | 320 |
| 6 | A2 | 9900 | 80 | I/IV | 5/20 | A1 | 15 | — | — | α | 320 |
| 7 | A3 | 9200 | 85 | V | 20 | A1/B1 | 15/5 | — | — | β | 320 |
| 8 | A5 | 9000 | 85 | V | 15 | A2/B4 | 15/5 | — | — | α | 320 |
| 9 | A8 | 8900 | 80 | V | 20 | A1/B1 | 20/5 | — | — | β | 320 |
| 10 | A5 | 9000 | 85 | V | 15 | A1/B2 | 15/10 | — | — | α | 320 |
| 11 | A8 | 8900 | 80 | V | 20 | B2 | 5 | S1 | 20 | α | 320 |
| 12 | A6 | 3700 | 100 | II/IV | 5/20 | A1 | 5 | — | — | α | 320 |
| 13 | A8 | 8900 | 80 | V | 5 | A2/B4 | 20/20 | — | — | β | 320 |
| 14 | A3 | 9200 | 80 | — | — | B2 | 25 | S2 | 20 | α/β | 256/64 |
| 15 | A3 | 9200 | 80 | — | — | A1/B1 | 20/30 | — | — | β | 320 |
| Comparative Examples | | | | | | | | | | | |
| 1 | A1 | 4300 | 100 | II/V | 7.5/20 | — | — | — | — | α | 320 |
| 2 | A4 | 4500 | 100 | III/V | 12.5/12.5 | — | — | S3 | 5 | α | 320 |
| 3 | A7 | 4000 | 100 | IV | 25 | — | — | — | — | α/β | 256/64 |

| | Properties of resist | | | | | |
|---|---|---|---|---|---|---|
| | Sensitivity (msec) | Resolution (μm) | Pattern shape | Remained thickness ratio (%) | Deveropability | Heat resistance (°C.) |
| Examples | | | | | | |
| 1 | 290 | 0.50 | Good | >99 | Good | 150 |
| 2 | 300 | 0.50 | Good | >99 | Good | 150 |
| 3 | 280 | 0.50 | Good | >99 | Good | 150 |
| 4 | 270 | 0.50 | Good | >99 | Good | 150 |
| 5 | 330 | 0.50 | Good | >99 | Good | 150 |
| 6 | 320 | 0.48 | Good | >99 | Good | 150 |
| 7 | 290 | 0.48 | Good | >99 | Good | 150 |
| 8 | 270 | 0.48 | Good | >99 | Good | 150 |
| 9 | 300 | 0.48 | Good | >99 | Good | 150 |
| 10 | 270 | 0.48 | Good | >99 | Good | 150 |
| 11 | 270 | 0.48 | Good | >99 | Good | 150 |
| 12 | 290 | 0.40 | Good | >99 | Good | 150 |
| 13 | 300 | 0.40 | Good | >99 | Good | 150 |
| 14 | 240 | 0.40 | Good | >99 | Good | 150 |
| 15 | 290 | 0.40 | Good | >99 | Good | 150 |
| Comparative Examples | | | | | | |
| 1 | 390 | 0.55 | Good | >99 | Scum exist at 0.50 μm | 150 |
| 2 | 380 | 0.55 | Reversely tapered | 96 | Scum exist at 0.50 μm | 145 |
| 3 | 290 | 0.45 | Pattern head | >99 | Scum exist at | 150 |

TABLE 1-continued

| | |
|---|---|
| rounded | 0.40 μm |

Notes:
[1] Addition amounts are in parts by weight.
[2] The quinone diazide compounds (III) to (V) are as follows:
III: Condensation product of 1 mol of 2,3,4-trihydroxybenzophenone and 3.0 mol of 1,2-naphthoquinonediazide-5-sulfonic acid chloride.
IV: Condensation product of 1 mol of 2,3,4,4'-tetrahydroxybenzophenone and 3.6 mol of 1,2-naphthoquinonediazide-5-sulfonic acid chloride.
V: Condensation product of 1 mol of 2,3,4,4'-tetrahydroxybenzophenone and 4.0 mol of 1,2-naphthoquinonediazide-5-sulfonic acid chloride.
[3] The dissolution accelerators are as follows:
S1: 1,1,1-tris(4-hydroxyphenyl)ethane
S2: 1,1-bis(4-hydroxyphenyl)-1-phenylethane
S3: an alkali-soluble novolak resin (Mw = 520) synthesized in the same manner as in Synthesis Example 1 except that 108.0 g (1.00 mol) of m-cresol, 20.3 g of a 37 wt. % aqueous solution of formaldehyde (formaldehyde: 0.25 mol) and 0.30 g (2.40 × 10⁻³ mol) of oxalic acid dihydrate were placed in a flask, and subjected to condensation for 30 minutes, with the temperature inside the flask maintained at 100° C.
[4] The kinds of solvents are as follows:
α: Ethyl cellosolve acetate.
β: Ethyl 2-hydroxypropionate.

We claim:

1. A radiation-sensitive resin composition comprising an admixture of an alkali-soluble resin and a compound having the following general formula [I]:

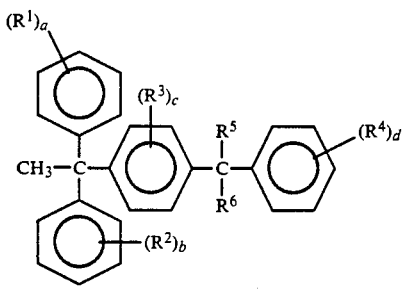

wherein $R^1$, $R^2$, $R^3$ and $R^4$ may be the same or different and each of $R^1$ to $R^4$ may comprise two or more different groups, and $R^1$ to $R^4$ are each a substituted or unsubstituted alkyl group, a substituted or unsubstituted aryl group or an OD group, wherein D is a hydrogen atom or an organic group containing a 1,2-quinonediazide group, at least one of $R^1$, $R^2$, and $R^4$ containing at least one OD group, at least one OD group in said compound containing a 1,2-quinonediazide group; $R^5$ and $R^6$ are each a hydrogen atom or a substituted or unsubstituted alkyl group; a, b and d are each an integer of from 0 to 5, provided that at least one of a, b and d is a positive integer corresponding to said OD group containing a 1,2-quinone diazide group; and c is an integer of from 0 to 4.

2. The composition according to claim 1, wherein the compound having the above general formula [I] comprises a compound having the general formula [I] in which c is 0.

3. The composition according to claim 2, wherein the compound having the above general formula [I] comprises a compound having the general formula [I] in which the groups $R^1$, $R^2$ and $R^4$ are each a substituted or unsubstituted alkyl group of up to 6 carbon atoms or an OD group, and the groups $R^5$ and $R^6$ are each a hydrogen atom or a substituted or unsubstituted alkyl group of up to 6 carbon atoms.

4. The composition according to claim 3, wherein the compound having the above general formula [I] comprises a compound having the general formula [I] in which the groups $R^1$, $R^2$ and $R^4$ are each a methyl group or an OD group, and the groups $R^5$ and $R^6$ are each a hydrogen atom or a methyl group.

5. The composition according to claim 1, wherein the compound having the above general formula [I] comprises a 1,2-quinonediazide sulfonate of one member selected from the group consisting of:
1,1-bis(4-hydroxyphenyl)-1-[4-(4-hydroxybenzyl)-phenyl]ethane,
1,1-bis(3,5-dimethyl-4-hydroxyphenyl)-1-[4-(4-hydroxybenzyl)phenyl]ethane,
1,1-bis(3,5-dimethyl-2-hydoxyphenyl)-1-[4-(4-hydroxybenzyl)phenyl]ethane,
1,1-bis(4-hydroxy-3-methylphenyl)-1-[4-(4-hydroxybenzyl)phenyl]ethane,
1,1-bis(2,6-dimethyl-4-hydroxyphenyl)-1-[4-(4-hydroxybenzyl)phenyl]ethane,
1,1-bis(3,4-dihydroxyphenyl)-1-[4-(4-hydroxybenzyl)-phenyl]ethane,
1,1-bis(3,4,5-trihydroxyphenyl)-1-[4-(4-hydroxybenzyl)phenyl]ethane,
1,1-bis(4-hydroxyphenyl)-1-[4-{1-(4-hydroxyphenyl)-1-methylethyl}phenyl]ethane,
1,1-bis(3,5-dimethyl-4-hydroxyphenyl)-1-[4-{1-(4-hydroxyphenyl)-1-methylethyl}phenyl]ethane,
1,1-bis(3,5-dimethyl-2-hydroxyphenyl)-1-[4-{1-(4-hydroxyphenyl)-1-methylethyl}phenyl]ethane,
1,1-bis(4-hydroxy-3-methylphenyl)-1-[4-{1-(4-hydroxyphenyl)-1-methylethyl}phenyl]ethane,
1,1-bis(2,6-dimethyl-4-hydroxyphenyl)-1-[4-{1-(4-hydroxyphenyl)-1-methylethyl}phenyl]ethane,
1,1-bis(3,4-dihydroxyphenyl)-1-[4-{1-(4-hydroxyphenyl)-1-methylethyl}phenyl]ethane,
1,1-bis(3,4,5-trihydroxyphenyl)-1-[4-(1-(4-hydroxyphenyl)-1-methylethyl}phenyl]ethane.

6. The composition according to claim 1, wherein the compound having the above general formula [I] is present in an amount of from 0.5 to 90 parts by weight per 100 parts by weight of the alkali-soluble resin.

7. The composition according to claim 1, which further comprises a 1,2-quinonediazide-sulfonic acid ester other than the compound having the above general formula [I].

8. The composition according to claim 7, wherein the 1,2-quinonediazide-sulfonic acid ester is present in an amount of from 3 to 100 parts by weight per 100 parts by weight of the alkali-soluble resin.

9. The composition according to claim 8, wherein the 1,2-quinonediazide-sulfonic acid ester is present in an amount such that the total amount of 1,2-quinonediazide-sulfonyl groups in the composition is from 5 to 25% by weight.

10. The composition according to claim 1, further comprising a dissolution accelerator.

11. The composition according to claim 10, wherein said dissolution accelerator comprises at least one member selected from the group consisting of 1,1-bis(4-hydroxyphenyl)-1-phenylethane, 1,1,1-tris(4-hydroxyphenyl)ethane, 3,5-dimethyl-4,4'-dihydroxydiphenylmethane, bisphenol A, 3,5-dimethyl-2',4-dihydroxydiphenylmethane, 1,1-bis(4-hydroxyphenyl)cyclohexane, 1,1-bis(4-hydroxyphenyl)-4-methylcyclohexane and alkali-soluble novolak resins having a weight average molecular weight in terms of polystyrene of 2,000 or less.

12. The composition according to claim 11, wherein said dissolution accelerator is present in an amount of up to 50 parts by weight per 100 parts by weight of the alkali-soluble resin.

* * * * *